United States Patent [19]

Query et al.

[11] Patent Number: 4,624,070
[45] Date of Patent: * Nov. 25, 1986

[54] METHOD AND COMPOSITION FOR PEST CONTROL USING ANESTHETIC AND INSECTICIDE

[76] Inventors: Grady W. Query, P.O. Box 34473, Charlotte, N.C. 28234; O. Grady Query, P.O. Box 1407, Charleston, S.C. 29402; H. Fred Kessler, 1722 E. 8th St., Charlotte, N.C. 28204

[*] Notice: The portion of the term of this patent subsequent to Aug. 13, 2002 has been disclaimed.

[21] Appl. No.: 738,410

[22] Filed: May 28, 1985

Related U.S. Application Data

[63] Continuation-in-part of Ser. No. 451,810, Feb. 1, 1983, Pat. No. 4,534,128.

[51] Int. Cl.[4] .............................................. A01M 7/00
[52] U.S. Cl. .......................................... 43/132.1; 71/3; 424/DIG. 10; 424/DIG. 12
[58] Field of Search ................. 43/132.1, 124; 424/43, 424/45, DIG. 10–DIG. 12; 71/3, 4, 85

[56] References Cited

U.S. PATENT DOCUMENTS 4,160,336  7/1979  Query et al. ...................... 43/132.1
4,534,128  8/1985  Query et al. ...................... 43/132.1

OTHER PUBLICATIONS

The Merck Index, 9th edition, 1976, by Windholz.

*Primary Examiner*—M. Jordan
*Attorney, Agent, or Firm*—B. Craig Killough

[57] ABSTRACT

A method and composition for treating pests and insects by combining an anesthetic and an insecticide into a mixture, and applying the mixture to the dwelling place of the insect or pest.

22 Claims, 5 Drawing Figures

U.S. Patent  Nov. 25, 1986  Sheet 1 of 2  4,624,070
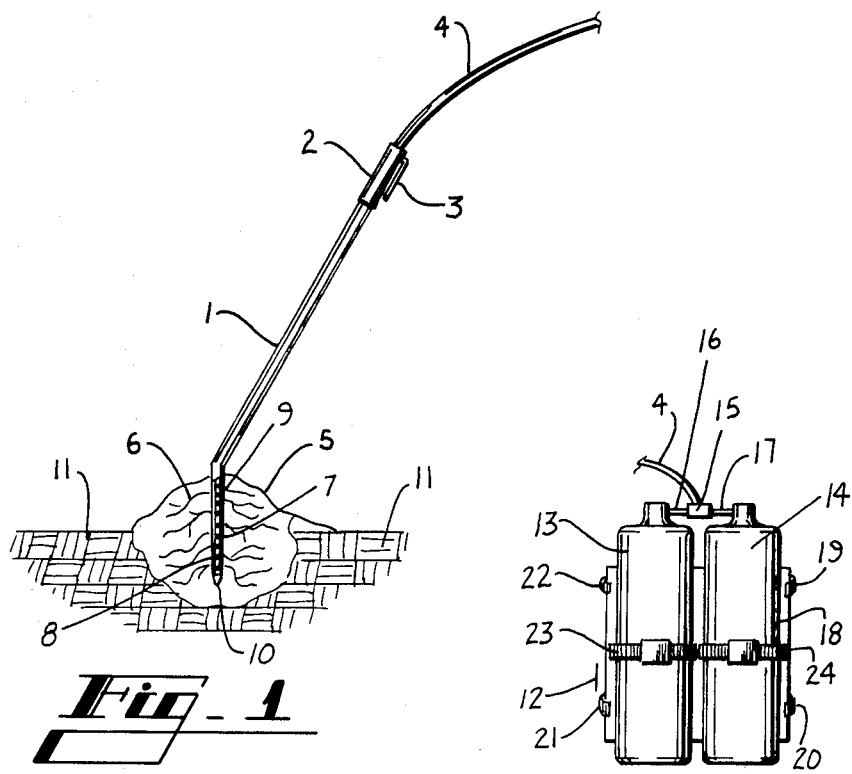
Fig. 1
Fig. 2
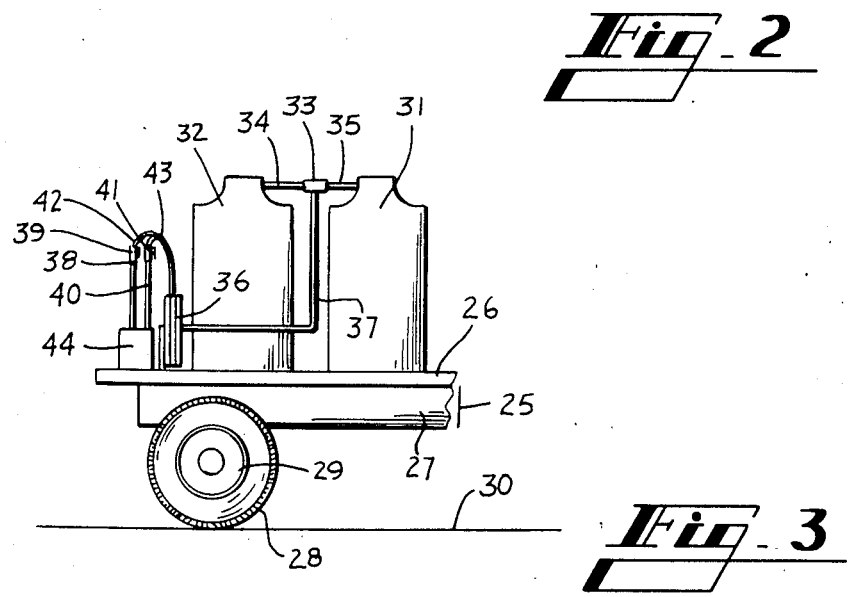
Fig. 3

METHOD AND COMPOSITION FOR PEST CONTROL USING ANESTHETIC AND INSECTICIDE

This application is a continuation in part of Ser. No. 06/451,810, filed Feb. 1, 1983 now U.S. Pat. No. 4,534,128 issued on Aug. 13, 1985.

BACKGROUND OF THE INVENTION

This invention relates to a mixture, method and apparatus for treating and controlling flying and crawling insects and pests, and more particularly to a method and apparatus which provides high efficacy with minimal danger to the user from attack by the insect by combining an anesthetic and an insecticide into a mixture so as to slow or stop the insect by means of the anesthetic while the insecticide acts to kill the insect.

In treating certain kinds of flying and crawling pests, the user is exposed to attack from the insect, resulting in bites or stings. Wasps and hornets may attack the user while the user is applying the insecticide agent. Fireants will react to any disturbance in the fireant mound and will attack the person who is applying insecticide. Fireants have a powerful and dangerous sting which is known to kill both animals and humans. They are very quick, and it is desirable to instantly immobilize these insects immediately upon treatment.

With other types of insects or pests, it is desirable to instantly immobilize these insects or pests. After being immobilized, an insecticide may be used to kill the flying or crawling insect or pest, aiding in control of the insects and pests.

An object of the present invention is a method of controlling crawling and flying insects and pests by using an anesthetic type immobilizing agent in combination with a residual or nonresidual insecticide, and delivering that combination into the nest, mound or dwelling place of the insect or pest, using a probing type spraying device.

Another object of the present invention is to immobilize the insect or pest immediately upon approaching the colony, nest or dwelling place in order to protect the person applying the method from attck by the insect or pest.

Still another object of the present invention is to apply an eradication mixture into a nest, colony or dwelling place under pressure thereby injecting the mixture deep into tunnels and chambers of a colony or nest or deep into cracks and crevices where insects may hide.

A further object of the invention is to anesthesize, immobilize and stun pests or insects immediately upon the application of the mixture in order to prevent the immediate removal of pupa, eggs or gueen, thereby preventing the establishment of a colony or nest elsewhere.

A still further object of the invention is to anethesize the flying or crawling insect or pest until the insecticide works to kill the insect or pest.

Another object of the invention is to anesthesize the insect or pest until residual insecticide can kill the insect or pest, with a residual type insecticide providing a long term kill in prevention of return to the nest, colony or dwelling place.

An additional object of the invention is to provide safety to the user or operator from stinging or biting insects, by using an anesthetic to instantly immobilize the stinging or biting pest.

A further additional object of the invention is to immediately anesthesize and immobilize the insect or pest to prevent further travel of the pest while an insecticide works to kill the insect or pest.

Yet another object of the invention is to reduce the amount of active insecticide which is placed in the atmosphere by immobilizing the insect near the nest, mound or dwelling place, thereby reducing the environmental and safety hazards of insecticide application.

These and other objects and features of the above mentioned will be apparent from the following description and appended claims.

SUMMARY OF THE INVENTION

Briefly, the invention is a method and apparatus for treating insects or pests in their nest, mound or dwelling place. An anesthetic is applied to the nest, mound or dwelling place, immobilizing the insect. An insecticide is mixed with the anesthetic, which will act to kill the insect or pest which has been immobilized by the anesthetic. The mixture may be injected in the nest, mound or dwelling place under pressure. The insecticide may be a quick killing nonresidual insecticide such as pyrethrum or a synthetic pyrethroid. The insecticide may be a residual type insecticide such as Dursban[1], Baygon[2], Baytex[2], or Vapona[3]. The anesthetic may be dimethyl ether. Pressure may be provided by a propellant added to a mixture. The propellant may be freon, dimethyl ether or carbon dioxide. Pressure may be provided by a pump. Pressure may be provided by adding steam to the mixture. The apparatus for use in treating the nsects or pests in the nest, mound or dwelling place may comprise a mixture of insecticide and an anesthetic; a plurality of storage tanks operate to hold the mixture; and injection means operative to remove the mixture from the storage tanks and to inject the mixture into the nest, mound or dwelling place. The mixture may further comprise a propellant, and the propellant may be a refrigerant. The plurality of storage tanks may be attached to a back pack device. The plurality of storage tanks may be attached to a trailer. The injection means may comprise a rod with a penetrating shaft and may be placed within the nest, mound or dwelling place; a control means operative to operate and control the flow through the rod; and hose means to connect the plurality of storage tanks with the rod. Multiple orifices may be placed near the end of the rod. Switch means may control the flow of the mixture from the plurality of the storage tanks when more than one storage tank is utilized. The control means may be a squeeze lever connected on a handle to the rod. The insecticide may be pyrethrum. The insecticide may be Dursban. The propellant may be freon, dimethyl ether or carbon dioxide. The refrigerant may be freon dimethyl ether or carbon dioxide. The anesthetic may be dimethyl ether.

[1]Registered trademark of Dow Chemical Company, Active Ingredient is Chlorpyrifos.
[2]Farben Fabricken Bayer GmbH, Levekusen, Germany
[3]Shell Oil Company

DESCRIPTION OF THE DRAWINGS

The invention will become more fully understood from the following detailed description and appended claims when taken with drawings:

FIG. 1 is a plain, partially sectioned view of rod 1 being inserted into ant hill or mound 5.

FIG. 2 is a plain view of a portable back pack device.

FIG. 3 is a plain view of a tank trailer 25 and holding tanks 31 and 32.

DETAILED DESCRIPTION OF THE PREFERRED EMBODIMENTS

Figure 5:
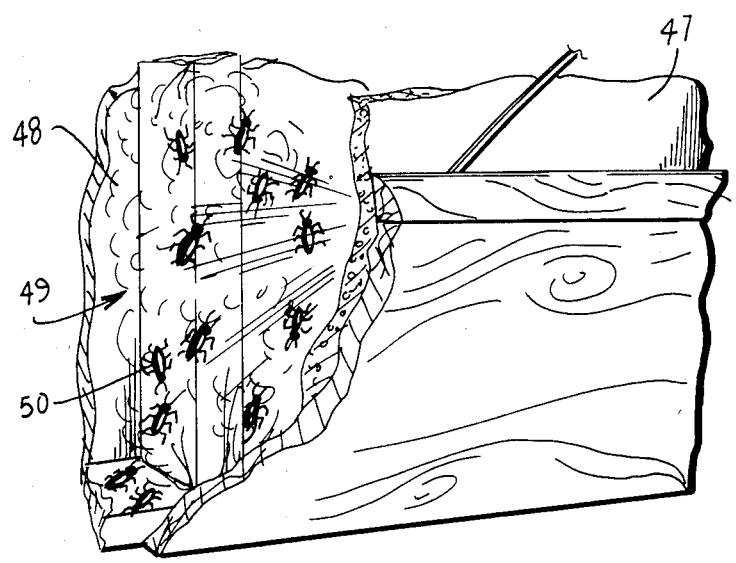
FIG. 5 is a partially sectioned view of a wall being treated for crawling insects.

Referring to the drawings, FIG. 1 is a plain, partially sectioned view of rod 1 being inserted into ant hill or mound 5. Rod 1 is shown having penetrating shaft 7 into an ant hill mound 5 is a fireant hill or mound in the ground 11. The fireant hill or mound 5 comprises many tunnels such as tunnel 6 and many chambers. The probing device, or rod 1, has a handle 2 in which there is a squeeze lever 3. Squeeze lever 3 controls the flow of the eradication combination through hose 4. Holes in penetrating shaft 7, such as hole 8 and hole 9, enable the eradication mixture flowing from hose 4 to be dispersed inside the ant hill or mound 5. The eradication mixture is dispersed under pressure deep inside the tunnels, such as tunnel 6. Solid pointed tip 10 of penetrating shaft 7 is useful in as an aid in probing into the ant hill or mound 5 and prevents dirt from entering through the tip of the penetrating shaft 7 and potentially clogging hole openings.

FIG. 2 is a plan view of a portable back pack device 12. This device may be worn by a person attempting to control or eradicate the insects or pests. Hose 4 is connected to a switching device 15. The switching device 15 controls through which tank, tank 13 or tank 14, the eradication mixture will be utilized. Connecting line 16 connects 13 to switching device 15. Connecting line 17 connects tank 14 to switching device 15. Tanks 13 and 14 are secured by tanks support strap 23 and tank support strap 25 to tank harness 18. Straps 19, 20, 21, and 22 are available to secure the tank harness 18 to a person carrying the back pack device 12.

FIG. 3 is a plain view of tank trailer 25 holding tanks 31 and 32. The eradication mixture may be stored in tanks 31 and 32. Line 34 connects tank 32 to switching device 33. Line 35 connects tank 31 to switching device 33. Switching device 33 performs a similar function to the switching device 15 of the pack pack device 12 shown in FIG. 2. Line 37 connects switching device 33 to a coil of hoses 36. From the coil of hoses 36, emanates hoses 42 and 43. Hose 42 connects coil 36 to the rod 38 with handle 39. Hose 43 connects coil 36 with rod 40 and handle 41. Rods 38 and 40 are stored in rod holding device 44. The tank trailer 25 shown in FIG. 3 shows two rods and, therefore, would be appropriate for two persons utilizing the method and apparatus of the invention. Other devices utilizing more rods are certainly within scope of this invention. Tank trailer 25 is shown with a trailer bed 26 upon which the tanks 31 and 32. Trailer frame 27 supports trailer bed 26.

Wheel 29 with tire 28 is secured to trailer frame 27 and gives a tank trailer 25 mobility. Any plurality of wheels and tires may be utilized. The tires, such as tire 28, support the tank trailer 25 on the ground 30.

Figure 4:
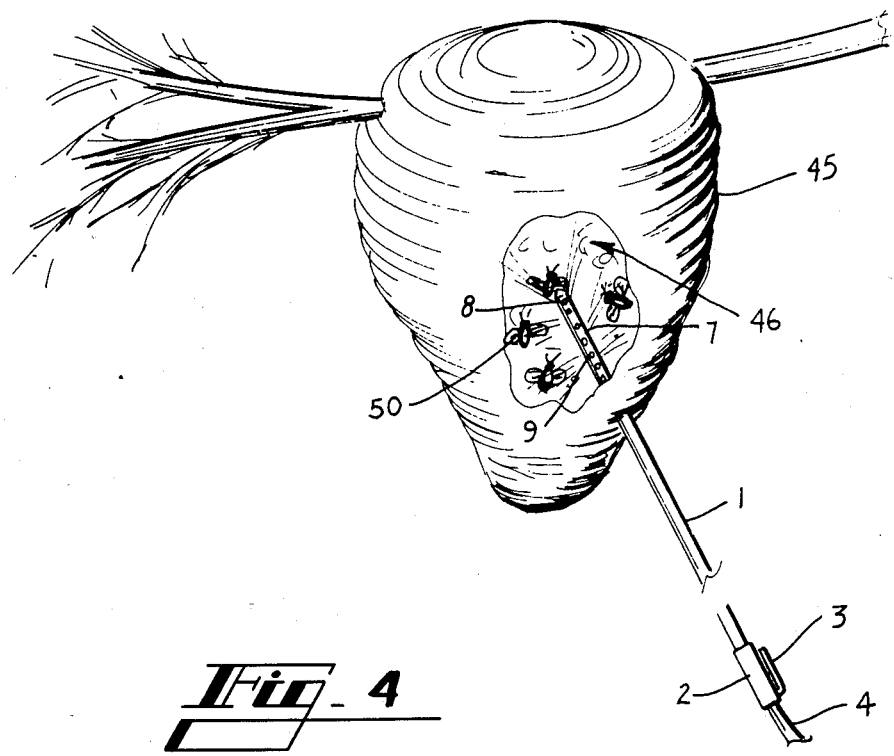
FIG. 4 is a plain, partially sectioned view of rod 1 being inserted into hornet's nest 45.

FIG. 4 is a plain, partially sectioned view of rod 1 being inserted into hornets nest 45. The hornets nest 45 comprises many inner chambers such as chamber 46. The probing device, or rod 1, has a handle 2 on which there is a squeeze lever 3. Squeeze lever 3 controls the flow of the eradication combination through the hose 4. Holes in the penetrating shaft 7, such as hole 8 and hole 9, enable the eradication mixture flowing from hose 4 to be dispersed inside the hornets nest 45.

FIG. 5 is a partially sectioned view of wall 47. The eradication combination is delivered in aerosol form 48 and seeps through cracks and crevices into inner chamber 49 of wall 47 and contacts insect 50, immobilizing and subsequently killing the insect.

The present invention includes the mixture resulting from the combination of an insecticide with an anesthetic. A propellant may also be added to the combination. The insecticide may be residual or nonresidual. The residual insecticide may be Dursban. The residual insecticide may be a carbamate, such as Baygon or Baytex, or other residual insecticide such as Vapona. The anesthetic may be dimethyl ether. The nonresidual insecticide may be pyrethrum or synthetic pyrethroid. The propellant may be a refrigerant. The refrigerant-propellant may be freon or dimethyl ether. Any other residual or nonresidual insectide other than Dursban or pyrethrum may be utilized. Any other propellant other than freon may be used. Any other refrigerant other than freon or dimethyl ether may be utilized. Any other anesthetic other than dimethyl ether may be utilized.

Various proportions of insecticides, dimethyl ether and inert ingredients have produced excellent results. Specifically, it has been found that combining a mixture of approximately 0.5% to 2.5% insecticide (as a percentage of the overall mixture) with a mixture of approximately two-thirds ($\frac{2}{3}$) dimethyl ether and one-third ($\frac{1}{3}$) inert ingredients produces excellent results. The inert ingredients may consist of the mixture of methylene chloride, petroleum oil (refined), piperonyl butoxide (technical) in the approximate ratios of 3 to 3 to 1 respectively when pyrethrums are used, with the piperonyl butoxide deleted when other insecticides are used. Specifically, a preferred mixture would have the following percentages by weight:

Insecticide: 0.5 to 2.5%
Petroleum oil (refined): 16.5%
Methylene Chloride: 16.5%
Dimethyl Ether: 64.5 to 66.5%

As indicated previously, the insecticide may be virtually any known insecticide material. The insecticide may be a non-residual insecticide such as pyrethrums or synthetic pyrethroids. Most specifically, the pyrethrums could be pyrethrins I and II. The residual insecticides could be organo phosphates, or carbamates. The specific organo phosphate could be chlophyrifos phosphorothioate, which is marketed commercially under the trademark Dursban. The carbamates could be specifically Baygon[4] or Baytex. The residual insecticide could be Vapona or Rotenone.

The insecticide such as Dursban or pyrethrum, is combined with the anesthetic such as dimethyl ether, or any other anesthetic, and may be further combined with freon, or any other refrigerant-propellant, and held under pressure in tanks 13 and 14 of backpack device 12, or tanks 31 and 32 of tank trailer 25. The pressurized combination, when injected through rods such as rods 1, 38 and 40 in the drawings, tends to immobilize, anesthesize and stun the insect or pest. The effect of the anesthetic is to anesthesize and immobilize the pest or insect immediately upon application, keeping the insect or pest from attacking, biting or stinging the person treating the insect or pest, while the insecticide acts to kill the insect or pest. The pressurized, aerosol form of delivery of the combination tends to move the combination rapidly through tunnels, chambers, cracks or crevices where the insect lives or hides, to give the total knock down capability and instant immobility of the insect or pest. Pressure relief valves and pressure regulators may be added to this system as desired, or as required by the user. The initial injection of the combination tends to anesthesize, stun and immobilize the insect or pest, protecting the person applying the combination from attacks by the insect or pests. The pressurized application takes advantage of forcing the combination into tunnels, chambers, cracks or crevices where the insect may live or hide. The insect or pest is stunned, immobilized and anesthesized, preventing the carrying off of pupae, eggs, queens, or fleeing of the insect. Subcolonies or runners are also reached through tunnels in the case of insects nesting in the ground. This invention has the capability of killing the queen or other reproductive members of the colony, including reproductive males, before they can escape. This invention can eliminate the insects or pests present in the mound or nest, and when used with a residual insecticide can kill those insects or pests returning to the nest or mound. The instant immobilizing capability can prevent insects or pests from leaving the nest or mound and escaping the residual or nonresidual insecticide. This is particularly effective when applied to wasps nests or hornets nests which tend to absorb the mixture. Wasps and hornets returning to the nest after application are subjected to the mixture absorbed by the nest.

⁴o-Isopropoxphenyl Methylcarbamate

While the invention has been described with reference to specific embodiment, the description is illustrative and is not to be construed as limiting the scope of the invention. Various modifications and changes may occur to those skilled in the art without departing from the scope of the invention as defined by the appended claims.

The anesthetic immediately immobilizes the insect or pest. It is faster acting in immobilizing the insect or pest than is the use of a combination of a refrigerant and quick kill insecticide alone. It is faster acting in immobilizing the insect or pest than is the use of pyrethrum alone. The anesthesized insect or pest is then killed by the residual or nonresidual insecticide which is delivered in combination with the anesthetic. Due to the instant immobilization of the insect or pest, more protection is given to the person applying the mixture from attack by a stinging or biting insect or pest. The instant immobilization, by eliminating fleeing from the mound, nest or dwelling place, reduces the area over which the insecticide must be applied. This reduces the adverse environmental consequences of insecticide distribution into the atmosphere, particularly where a residual insecticide is used.

Compressed air, or carbon dioxide can be applied to the mixture containers during application during cold weather to increase the pressure under which the mixture is applied to the mound, nest or hiding place of the insect or pest.

The mixture may be packaged in containers of any size.

Other types of anesthetic using the same method and apparatus as disclosed herein can be utilized.

Other modifications and changes may occur to those skilled in the art without departing from scope of the invention as defined by the appended claims.

What is claimed is:

1. A method of treating insects or pests, comprising:
 a. combining a mixture of approximately 0.5% to 2.5% insectide with the balance of the mixture being approximately two-thirds dimethyl ether as an anesthetic and one-third inert ingredients; and
 b. applying said mixture onto a nest or dwelling place of said insects or pests or onto the insects or pests themselves whereby said anesthetic reduces the mobility of said insects or pests while said insecticide acts to kill said insects or pests.

2. A method as described in claim 1, wherein said inert ingredients are methylene chloride and petroleum oil (refined) in equal proportions.

3. A method of treating insects or pests, comprising:
 a. combining an insecticide and an anesthetic into a mixture as follows:

| Insecticide | .5 to 2.5% |
|---|---|
| Petroleum Oil, Refined | 16.5% |
| Methyl Chloride | 16.5% |
| Dimethyl Ether | 64.5 to 66.5% |
| | 100% | where the percentages indicated are by weight; and
 b. applying said mixture onto a nest or dwelling place of said insects or pests or onto the insects or pests themselves whereby said anesthetic reduces the mobility of said insects or pests while said insecticide acts to kill said insects or pests.

4. A method as described in claim 3, wherein said insecticide is an organo phosphate.

5. A method as described in claim 3, wherein said insecticide is a carbamate.

6. A method as described in claim 3, wherein said insecticide is a synthetic pyrethroid.

7. A method as described in claim 3, wherein said insecticide is Pyrethrins I and II.

8. A method as described in claim 3, wherein said insecticide is Vapona.

9. A method as described in claim 4, wherein said organo phosphate is chlorphyrifos phosphorothioate.

10. A method as described in claim 5, wherein said carbamate is Baygon.

11. A method as described in claim 5, wherein said carbamate is Baytex.

12. A mixture which is used to treat insects or pests, wherein an anesthetic is combined in the mixture to immobilize the insect, and an insecticide is combined in the mixture to kill the insect, comprising approximately 0.5% to 2.5% insecticide as a percentage of the overall mixture, with the balance of the mixture being approximately two-thirds (⅔) dimethyl ether as an anesthetic and one-third (⅓) inert ingredients by weight.

13. A mixture as described in claim 12, wherein said inert ingredients are methylene chloride and an petroleum oil (refined), in equal proportions.

14. A mixture which is used to treat insects or pests, wherein an anesthetic is combined in the mixture to immobilize the insect, and an insecticide is combined in the mixture to kill the insect, comprising:

| Insecticide | .5 to 2.5% |
|---|---|
| Petroleum Oil, Refined | 16.5% |
| Methyl Chloride | 16.5% |
| Dimethyl Ether | 64.5 to 66.5% |
| | 100% | where the percentages indicated are by weight.

15. A mixture as described in claim 14, wherein said insecticide is an organo phosphate.

16. A mixture as described in claim 14, wherein said insecticide is a carbamate.

17. A mixture as described in claim 14, wherein said insecticide is a synthetic pyrethroid.

18. A mixture as described in claim 14, wherein said insecticide is pyrethrins I and II.

19. A mixture as described in claim 14, wherein said insecticide is Vapona.

20. A mixture as described in claim 15, wherein said organo phosphate is chlophyrifos phosphorothioate.

21. A mixture as described in claim 16, wherein said carbamate is Baygon.

22. A mixture as described in claim 16, wherein said carbamate is Baytex.

* * * * *